United States Patent
Blanton et al.

(10) Patent No.: US 7,321,036 B2
(45) Date of Patent: *Jan. 22, 2008

(54) PROCESS FOR PREPARING ALUMINUM TRISQUINOLINE COMPLEX

(75) Inventors: Thomas N. Blanton, Rochester, NY (US); Manju Rajeswaran, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 663 days.

This patent is subject to a terminal disclaimer.

(21) Appl. No.: 10/834,827

(22) Filed: Apr. 29, 2004

(65) Prior Publication Data

US 2005/0261519 A1    Nov. 24, 2005

(51) Int. Cl.
C07D 401/14 (2006.01)
C07D 215/30 (2006.01)

(52) U.S. Cl. .............................. 546/7; 546/6; 546/178
(58) Field of Classification Search .................... 546/7, 546/6, 178
See application file for complete search history.

(56) References Cited

U.S. PATENT DOCUMENTS 7,169,484 B2 * 1/2007 Rajeswaran et al. ........ 428/690

FOREIGN PATENT DOCUMENTS

| JP | 4-85388 | 3/1992 |
| JP | 4-206296 | 7/1992 |
| WO | 03/106422 | 12/2003 |

OTHER PUBLICATIONS

Brinkmann, M., et al., "Correlation Between Molecular Packing and Optical Properties in Different Crystalline Polymorphs and Amorphous Thin Films of mer-Tris(8-hydroxyquinoline)aluminum(III)", J. Am. Chem. Soc., 2000, pp. 5147-5157.
Cölle, M., et al., "Preparation and Characterization of Blue-Luminescent Tris(8-hydroxyquinoline)aluminum ($Alq_3$), Advanced Functional Materials", 2003, pp. 108-112.
Rajeswaran, M., et al., "Refinement of the Crystal Structure of the δ-modification of tris(8-hydroxyquinoline)aluminum(III), δ-$Al(C_9H_6NO)_3$, the blue luminescent $Alq_3$", Z Kristallogr. NCS 218 (2003), pp. 1-2.
Rajeswaran, M., et al., "Process for Forming a Composite Including an Aluminum Trisquinoline Complex", USSN 10/834621, filed Apr. 29, 2004.

* cited by examiner

Primary Examiner—Charanjit S. Aulakh
(74) Attorney, Agent, or Firm—Arthur E. Kluegel (57) ABSTRACT

A process for forming the facial isomer of an aluminum trisquinoline complex comprises heating the solid aluminum trisquinoline complex material at a temperature at least 50° C. below the melting point temperature of the solid for a time sufficient to convert the aluminum trisquinoline complex to at least 99 mol % of one polymorph of the facial-isomer that fluoresces with a maximum intensity below 510 nm.

19 Claims, 4 Drawing Sheets

PROCESS FOR PREPARING ALUMINUM TRISQUINOLINE COMPLEX

FIELD OF THE INVENTION

This invention relates to the formation of solid forms of an aluminum trisquinoline complex that emit blue light at low processing temperatures.

BACKGROUND OF THE INVENTION

Tris(2-methyl-8-quinolinolato)aluminum(III), $Alq_3$, has been used extensively in electroluminescent devices (EL) because of its ability to transport electrons. It has been used as a yellow-green emissive material as well as a host for emissive dopants.

While organic EL devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", *RCA Review*, 30, 322-334, (1969); and Dresner U.S. Pat. No. 3,710,167, issued Jan. 9, 1973. The organic layers in these devices, usually composed of a polycyclic aromatic hydrocarbon, were very thick (much greater than 1 µm). Consequently, operating voltages were very high, often greater than 100V.

More recent organic EL devices include an organic EL element consisting of extremely thin layers (e.g., less than 1.0 µm) between the anode and the cathode. Herein, the term "organic EL element" encompasses the layers between the anode and cathode. Reducing the thickness lowered the resistance of the organic layer and has enabled devices that operate at much lower voltage. In a basic two-layer EL device structure, described first in U.S. Pat. No. 4,356,429, one organic layer of the EL element adjacent to the anode is specifically chosen to transport holes, and therefore, it is referred to as the hole-transporting layer, and the other organic layer is specifically chosen to transport electrons, and is referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al (*J. Applied Physics*, 65, Pages 3610-3616, (1989)). The light-emitting layer commonly consists of a host material doped with a guest material, also known as a dopant. Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

Since these early inventions, further improvements in device materials have resulted in improved performance in attributes such as color, stability, luminance efficiency and manufacturability, e.g., as disclosed in U.S. Pat. Nos. 5,061,569 5,409,783, 5,554,450, 5,593,788, 5,683,823, 5,908,581, 5,928,802, 6,020,078, and 6,208,077, amongst others.

Notwithstanding these developments, there are continuing needs for organic EL device components, such as light-emitting materials that will provide high luminance efficiencies combined with high color purity and long lifetimes.

Figure 1:
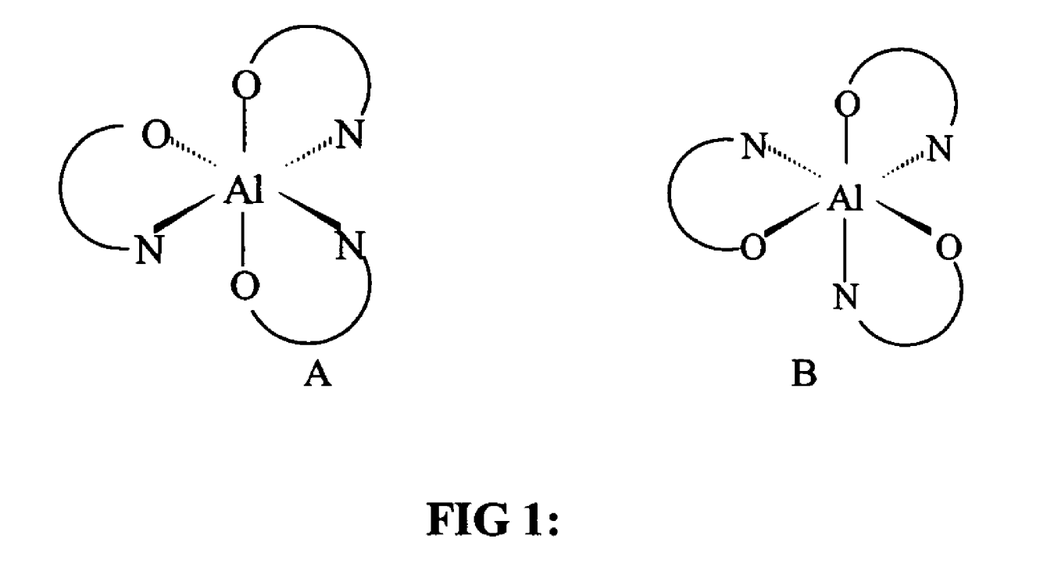
FIG. 1 shows a representation of the meridional (A) and facial (B) isomers of Alq$_3$.

Tris-chelated octahedral complexes, such as $Alq_3$, can exist in the facial or meridional isomeric forms. FIG. 1 show a simple representation of the meridional-isomer (A) and the facial-isomer (B). The meridional isomer of $Alq_3$ commonly crystallizes in either of two polymorphs often called the β- or ε-phases. These forms will be referred to as β- and ε-$Alq_3$. The ε-phase of $Alq_3$ was discovered in studies associated with this disclosure.

Until very recently, only the meridional form of $Alq_3$ had been fully characterized, although, M. Yasushi, S. Kenji, U. Taeko (JP 2902745) and S. Kenji, K. Yasushi, U. Taeko, M. Yasushi, (JP 2823352) had reported a green emitting $Alq_3$ structure that they initially proposed as a facial isomer.

The α form of $Alq_3$, referred to as α-$Alq_3$, was originally believed to be composed of only the meridional isomer. Single crystal X-ray diffraction studies carried out as part of the studies associated with this disclosure have indicated that crystals of the α form of $Alq_3$ contain both the facial and meridional isomers. The α form of $Alq_3$, emits yellow-green light.

Only recently the facial-isomer of δ-$Alq_3$ has been identified and completely characterized and this form of $Alq_3$ emits blue light. Two phases (δ and γ) of $Alq_3$ that can be formed at higher temperatures have been characterized using X-ray diffraction technique as the primary characterization method. ["Refinement of the Crystal Structure of the δ-Modification of tris(8-hydroxyquinoline) Aluminum(III), —$Al(C_9H_6NO)_3$, the blue luminescent $Alq_3$: Manju Rajeswaran, Thomas N. Blanton and Kevin P. Klubek, *Z. Kristallogr. NCS* 218, 439-440, 2003.] Recently M. Colle, J. Gmeiner, W. Milius, H. Hillebrecht, and W. Brutting, *Adv. Funct. Mater.*, 13, 108 (2003) have also reported the δ form of $Alq_3$. Colle and co-workers report that for annealing temperatures up to 365° C., samples of α-$Alq_3$ are a yellowish-green powder with a photoluminescence maximum of 506 nm. After an exothermic transition at about 380° C. they report the formation of the blue-light emitting $Alq_3$.

The facial isomer of δ-$Alq_3$ is very interesting due to its blue emission since it is known that other colors, such as green and red emission can be obtained from blue emitting materials by means of energy transfer to the appropriate dopant. However it has been very difficult to produce $Alq_3$ in the facial form in large quantities and in a pure form. Purity is important since in certain cases, when the facial isomer of $Alq_3$ is mixed with the meridional isomer in a continuous film, energy transfer can occur from the blue emitting form to the green emitting phase resulting in a less desirable green emission by the mixture. It would also be desirable to have a process for producing only one polymorph of the facial isomer of $Alq_3$ since it is known that polymorphs can have different physical properties and this can lead to problems in manufacturing a consistent product.

Recently M. Muccini and co-workers (WO 2003/106422) also described a process for the preparation of the facial isomer of $Alq_3$ as a mixture of two polymorphs, the γ and δ-phases of $Alq_3$, by heating the crystalline α-phase to very high temperatures. They report that by heating the α phase of $Alq_3$ at a temperature equal to or higher than 350° C. but lower than 420° C. it is possible to obtain a mixture of γ- and δ-$Alq_3$. However, they also report that, starting from the α-phase of $Alq_3$, the solid state transformation of meridional-isomer into facial-isomer occurs only near 390° C.

They describe heating commercial α-Alq$_3$ to 395° C. to form a mixture of γ and δ-Alq$_3$ wherein the ratio of γ-phase to the δ-phase is about 10/1 and that this is not significantly changed by differences in heating and cooling rates or by heating at a temperature of 410° C. instead of 395° C.

It is a problem to be solved to provide an economical process for forming the facial form of an aluminum trisquinoline complex, such as Alq$_3$, that would not require extremely high temperatures and that would provide material of high purity that emits blue light upon application of a potential.

SUMMARY OF THE INVENTION

The invention provides a process for forming the facial isomer of an aluminum trisquinoline complex comprising heating the solid aluminum trisquinoline complex material at a temperature at least 50° C. below the melting point temperature of the solid for a time sufficient to convert the aluminum trisquinoline complex to at least 99 mol % of one polymorph of the facial-isomer that fluoresces with a maximum intensity below 510 nm.

DETAILED DESCRIPTION OF THE INVENTION

As described in the summary, a process for forming one polymorph of the facial phase of an aluminum trisquinoline complex, which emits blue light, comprises heating the solid material at a temperature at least 50° C. below the melting point temperature of the solid for a time sufficient to convert the aluminum trisquinoline complex to at least 99 mol % of one polymorph of the facial-isomer. Desirably the solid material may be heated at 60° C., 70° C. or even 80° C. below the melting point temperature. The lower temperatures are more economical to achieve. Suitably, the heating temperature is not more than 150° C. below the melting point, because in this case it may take too much time to effect the conversion to the facial-isomer.

The melting point temperature is the temperature at which the solid phase of the aluminum trisquinoline complex converts to the liquid phase. Some aluminum trisquinoline complexes may decompose before they melt. In this case, the melting point temperature refers to the temperature at which a substantial amount of the complex decomposes, for example, the temperature at which 10% or more of the complex decomposes. That is, the temperature at which 10% or more of the material is no longer an aluminum trisquinoline complex.

Suitably the facial-isomer formed fluoresces with a maximum intensity in the blue or blue-green region of the spectrum. That is, when exposed to UV-light the facial-isomer emits light that is predominantly blue or blue-green in color. Blue light is generally defined as having a wavelength range in the visible region of the electromagnetic spectrum of 450-480 nm, blue-green light being in the range of 480-510 nm, and green 510-550 nm, green-yellow 550- 570 nm, as defined by Dr. R. W. G. Hunt in *The Reproduction of Colour in Photography, Printing & Television,* 4$^{th}$ Edition 1987, Fountain Press, page 4. For the purposes of this disclosure, visible light below 510 nm will be referred to as blue light. In one suitable embodiment the facial-isomer formed fluoresces with a maximum intensity below 510 nm and desirably below 500 nm.

The conversion of the aluminum trisquinoline complex to the facial-isomer may be monitored. X-ray powder diffraction (XRPD) is useful monitoring technique that can be used to determine the nature of isomers and polymorphism of an aluminum trisquinoline complex.

The monitoring process may be used to determine the heating time; once conversion to at least 99 mol % of a single polymorph of the facial isomer is achieved, heating may be discontinued. Typically, heating time will be in the range of 0.5 to 48 h and commonly 1 h to 24 h.

In one embodiment the aluminum trisquinoline complex is represented by Formula (1).

(1)

In Formula (1) the three quinoline groups may be the same or different. Each r$^1$ and r$^2$ represents an independently selected substituent. Examples of substituents are alkyl groups, such as a methyl group or aryl groups, such as a phenyl group or a tolyl group. Each n and m is independently 0-3. In one embodiment the quinoline groups, of Formula (1), do not have an r$^1$ substituent α to the N atom. Illustrative compounds of Formula (1) are listed below.

Ia (AlQ3)

1b

1c

In one desirable embodiment each $r^1$ and $r^2$ represents hydrogen and the aluminum trisquinoline complex comprises tris(2-methyl-8-quinolinolato)aluminum(III), Alq$_3$. Based on data from differential scanning calorimetry (DSC), the melting point temperature of Alq$_3$ has been determined to be about 417° C. In one desirable embodiment, the process includes heating a sample at Alq$_3$ below 367° C. for a sufficient time to convert Alq$_3$ to at least 99 mol % the δ-phase of the facial-isomer of Alq$_3$. Suitably, the process is carried out at a temperature below 360° C. or even below 350° C. Desirably the δ-phase of the facial-isomer of Alq$_3$ fluoresces in the blue or blue-green region of the spectrum.

Figure 2:
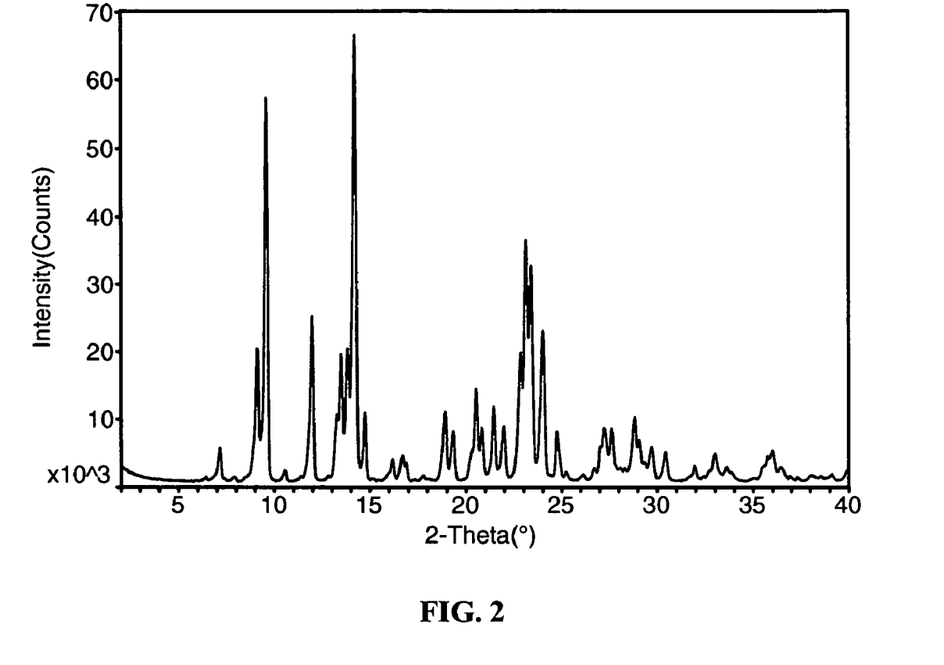
FIG. 2 shows the X-ray diffraction pattern for β-Alq$_3$.
Figure 3:
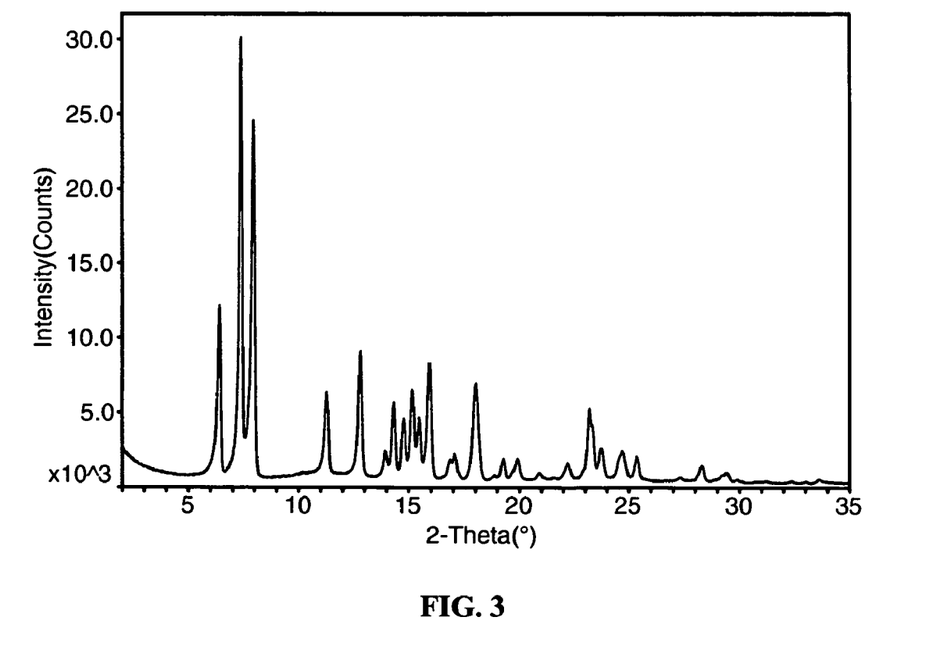
FIG. 3 shows the X-ray diffraction pattern for α-Alq$_3$.
Figure 4:
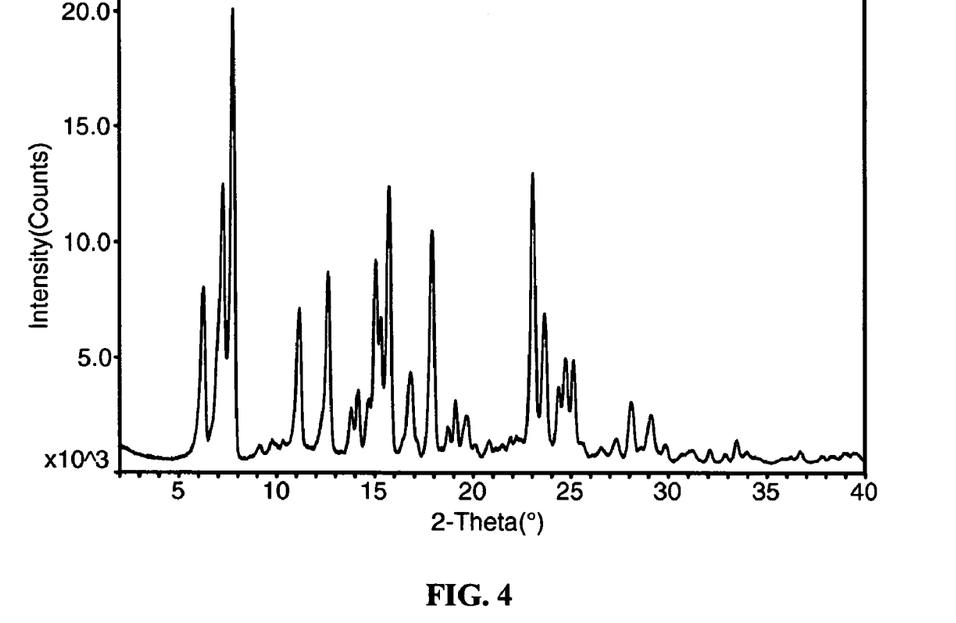
FIG. 4 shows the X-ray diffraction pattern for ε-Alq$_3$.
Figure 5:
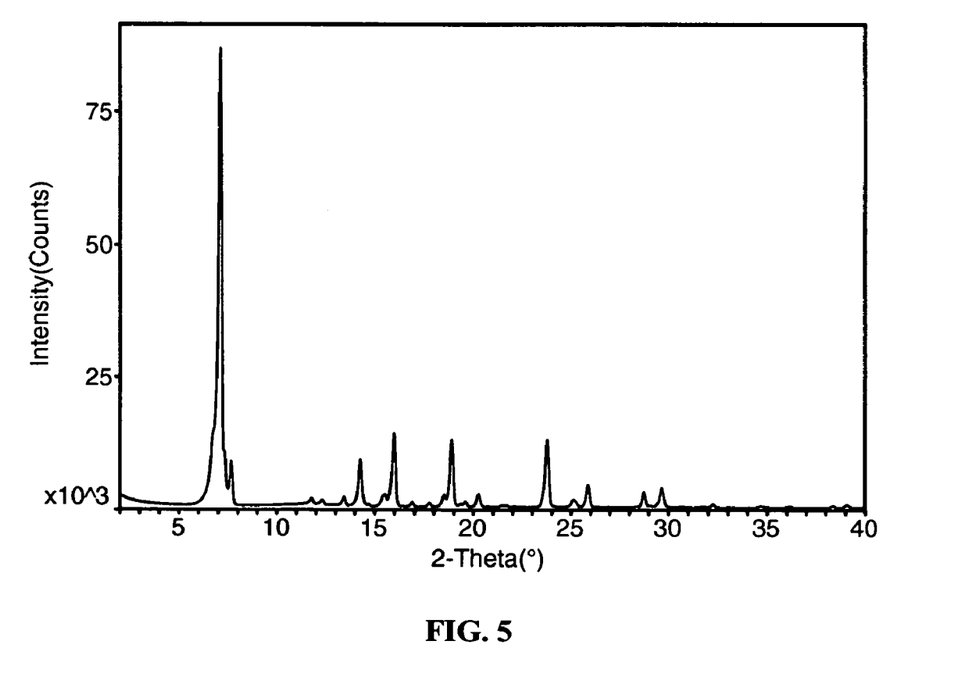
FIG. 5 shows the X-ray diffraction pattern for γ-Alq$_3$.
Figure 6:
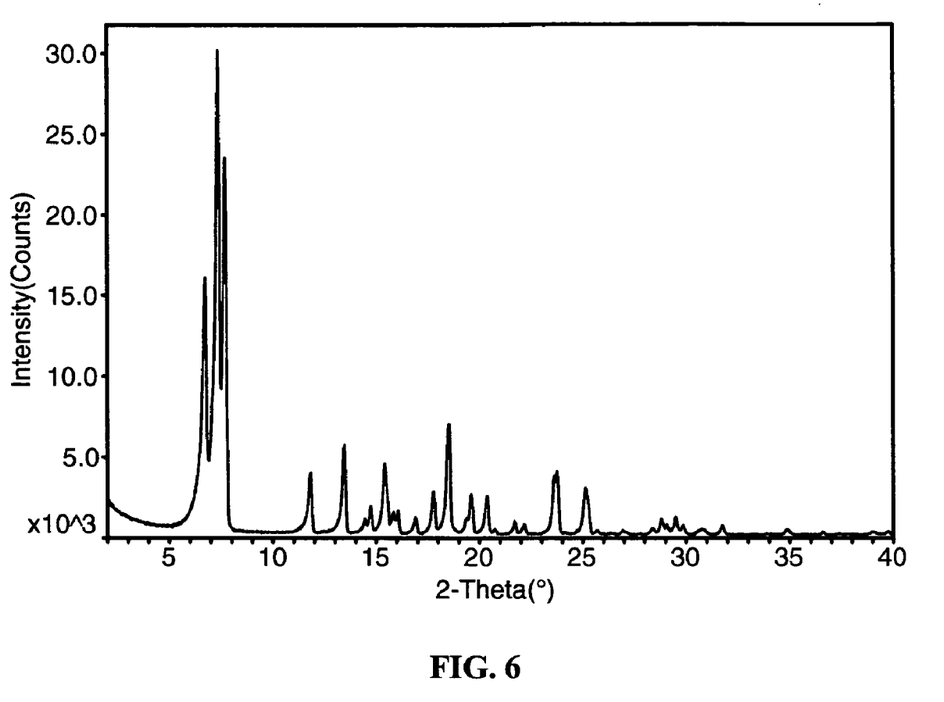
FIG. 6 shows the X-ray diffraction pattern for δ-Alq$_3$.

X-ray powder diffraction (XRPD) may be used to monitor the conversion of Alq$_3$ to the δ-phase. The X-ray powder diffraction patterns are shown for the β- (FIG. 2), α- (FIG. 3), ε- (FIG. 4), γ- (FIG. 5) and δ- (FIG. 6) forms of Alq$_3$. The five phases of Alq$_3$ can be identified by XRPD based on the 2-theta position of the diffraction peaks, in particular the diffraction peaks that are observed up to 11 degrees 2-theta are particularly useful in phase identification. Table 1 below highlights peaks useful in Alq$_3$ phase identification. These peak positions are based on the use of CuKα radiation and can vary up to 0.5 degrees 2-theta in exact position depending on instrument alignment and sample preparation.

TABLE 1

X-ray diffraction peaks useful in Alq$_3$ phase identification

| Alq$_3$ Phase | High Intensity Diffraction Peaks for Phase Identification 2-theta Position (degrees) | Low Intensity Diffraction Peaks for Phase Identification 2-theta Position (degrees) |
|---|---|---|
| β | 9.1, 9.6 | 7.2 |
| α | 6.4, 7.4, 7.9 | |
| ε | 6.4, 7.0, 7.4, 7.9 | 9.1, 9.8, 10.0, 10.3 |
| γ | 7.1 | |
| δ | 6.7, 7.4, 7.7 | |

In another embodiment, a process for forming the facial isomer of an aluminum trisquinoline complex comprises heating the solid material at a temperature of 70° C. or more below the melting point temperature of the solid for a time sufficient to convert the aluminum trisquinoline complex at least partially to the facial isomer. Desirably the solid is heated at 80° C., 90° C. or even 100° C. below the melting point temperature of the solid. In one embodiment, the solid is heated at a temperature more than 70° C. below the melting point temperature of the solid until the solid fluoresces in the blue or blue-green region of the spectrum when exposed to ultraviolet light. In another desirable embodiment the solid is heated for a sufficient time to convert the aluminum trisquinoline complex to at least 99 mol % of the facial isomer. Suitably the facial-isomer formed fluoresces with a maximum emission below 510 nm and desirably below 500 nm. The facial isomer may have more than one polymorph. Desirably, heating is continued until the facial isomer is present in only one polymorph.

In one embodiment the aluminum trisquinoline complex comprises tris(2-methyl-8-quinolinolato)aluminum(III), Alq$_3$. Suitably, one embodiment of the invention includes a process whereby a solid sample of Alq$_3$ is heated at a temperature below 350° C., below 340° C. or even below 330° C. for a sufficient time to form the facial-isomer of AlQ$_3$. Desirably the facial-isomer formed fluoresces with a maximum in the blue or blue-green region of the spectrum. Suitably, in one embodiment the solid sample of Alq$_3$ is heated above 300° C. but below 350° C. In another embodiment the facial isomer formed by heating a solid sample of Alq$_3$ at a temperature below 350° C. may exist as a mixture of the δ-phase and γ-phases of Alq$_3$. Typically heating of the solid sample continues for a sufficient time until blue light is emitted from the solid upon excitation by an ultraviolet light source. Suitably, the process is monitored, and heating continues until at least 99 mol % of a mixture comprising the δ-phase and γ-phase of Alq$_3$ is formed. In one embodiment, heating is continued further until at least 99 mol % of a mixture comprising the δ-phase of Alq$_3$. Desirably, the process is monitored using X-ray powder diffraction to analyze a representative portion of the sample and from this analysis determining the composition of the sample.

The invention and its advantages can be better appreciated by the following examples.

A series of Alq$_3$ powders were thermally processed. The purpose of the thermal processing was to generate samples of Alq$_3$ powders that would emit blue or blue-green light. The β-form of Alq$_3$ was used as the starting material for all thermal processing experiments. The term sample will be used to describe an aliquot of Alq$_3$ powder. Thermal processing, or annealing, of samples was performed using a Rigaku high temperature diffractometer stage. All thermal processing occurred in a dry N$_2$ ambient. The heating element was a platinum strip. The temperature was monitored using a platinum/rhodium thermocouple. An aliquot of commercial Alq$_3$ powder (Eastman Kodak Company) was placed on the heating strip and covered with beryllium foil. The beryllium prevents the Alq$_3$ powder from subliming during annealing process. Samples were thermally processed to a specified temperature cycle then cooled to room temperature, which was 20-22° C. The post processed samples were adhered to the beryllium foil, removed from the beryllium by gentle scraping, and the thermally processed powder samples were collected for phase and emission characterization. Visible light color emission for each sample was measured using a VWR UV light source, UV emission wavelength of 365 nanometers (nm). X-ray diffraction (XRD) was used for phase characterization using a Rigaku D2000 Bragg-Brentano diffractometer equipped with a Copper rotating anode. XRD data were collected during thermal processing with a linear position sensitive detector and after thermal processing with a scintillation detector.

SAMPLE 1: COMPARATIVE EXAMPLE 1

Commercial $Alq_3$ powder, with no thermal processing or annealing cycle, was analyzed by XRD for phase identification and exposed to 365 nm UV light for evaluation of visible light color emission. XRD phase identification determined that the sample was $\beta$-$Alq_3$. Comparative Example 1 demonstrates yellow-green emission upon UV light excitation and does not demonstrate any observed blue emission.

SAMPLE 2: COMPARATIVE EXAMPLE 2

Commercial $Alq_3$ powder was placed on a platinum heating strip and thermally processed. The annealing cycle began at 20° C., and the sample was heated at a rate of 10° C./min to 350° C., held at 350° C. for 5 minutes, and then cooled at a rate of 50° C./min to 20° C. The thermally processed powder was analyzed by XRD for phase identification and exposed to 365 mn UV light for evaluation of visible light color emission. XRD phase identification, after thermal processing indicated that $\epsilon$-$Alq_3$ had formed. Light emission from a 365 nm excitation was yellow-green. This process does not form a phase of $Alq_3$ that emits blue light.

SAMPLE 3: COMPARATIVE EXAMPLE 3

Commercial $Alq_3$ powder was placed on a platinum heating strip and thermally processed. The annealing cycle began at 20° C., the sample was heated at a rate of 10° C./min to 390° C., held at 390° C. for 5 minutes, and then cooled at a rate of 50° C./min to 20° C. The thermally processed powder was analyzed by XRD for phase identification and exposed to 365 nm UV light for evaluation of visible light color emission. XRD phase identification, after thermal processing indicated that a mixture of $\gamma$-phase and $\delta$-phase $Alq_3$ had formed. A 365 nm excitation exposure of the sample produced blue light emission, however the sample consists of a mixture of two phases of $Alq_3$.

EXAMPLE 4: COMPARATIVE EXAMPLE 4

Commercial $Alq_3$ powder was placed on a platinum heating strip and thermally processed. The annealing cycle began at 20° C.; the sample was heated at a rate of 10° C./min to 350° C. and held at 350° C. for 5 minutes. The sample was cooled at a rate of 50° C./min to 20° C. The sample was then heated at a rate of 10° C./min to 365° C. and held at 365° C. for 1 minute. The sample was cooled at a rate of 50° C./min to 20° C. The thermally processed powder was analyzed by XRD for phase identification and exposed to 365 nm UV light for evaluation of visible light color emission. XRD phase identification, after thermal processing indicated that a mixture of $\gamma$-phase and $\delta$-phase $Alq_3$ had formed. A 365 nm excitation exposure of the sample produced blue light emission, however the sample consists of a mixture of two phases of $Alq_3$.

SAMPLE 5: COMPARATIVE EXAMPLE 5

Commercial $Alq_3$ powder was placed on a platinum heating strip and thermally processed. The annealing cycle began at 20° C.; the sample was heated at a rate of 10° C./min to 350° C. The sample was then heated at a rate of 1° C./min to 390° C. The sample was then cooled at a rate of 50° C./min to 20° C. XRD analysis, after thermal processing, indicated that a mixture of the $\gamma$-phase and $\delta$-phase $Alq_3$ had formed. A 365 nm excitation exposure of the sample produced blue light emission, however the sample consists of a mixture of two phases of $Alq_3$.

SAMPLE 6: INVENTIVE EXAMPLE 1

Commercial $Alq_3$ powder was placed on a platinum heating strip and thermally processed. The annealing cycle began at 20° C., the sample was heated at a rate of 10° C./min to 345° C., held at 345° C. for 20 hours, and then cooled at a rate of 50° C./min to 20° C. XRD data were collected at 345° C. at time intervals of 0 min, 5 min, 15 min, 30 min, 1 h, followed by every hour up to 20 h. From analysis of the XRD data it could be determined that the onset of $\delta$-phase $Alq_3$ formation began at 30 min into the 345° C. processing. After thermally processing the powder for 20 h it was analyzed by XRD for phase identification and exposed to 365 nm UV light for evaluation of visible light color emission. XRD phase identification, indicated the formation of only pure $\delta$-phase $Alq_3$. Visible light color emission from a 365 nm excitation was blue. Inventive Example 1 demonstrates the formation of $\delta$-phase facial-$Alq_3$ in greater than 99% purity at a low processing temperature.

SAMPLE 7: INVENTIVE EXAMPLE 2

Commercial $Alq_3$ powder was placed on a platinum heating strip and thermally processed. The annealing cycle began at 20° C., the sample was heated at a rate of 10° C./min to 365° C., held at 365° C. for 20 hours, and then cooled at a rate of 50° C./min to 20° C. XRD data were collected at 365° C. at time intervals of 0 min, 5 min, 15 min, 30 min, and 1 h, followed by every hour up to 20 h. From analysis of the XRD data it could be determined that the onset $\delta$-$Alq_3$ formation began at 5 min into the 365° C. processing. After 20 h, XRD phase identification indicated that only $\delta$-$Alq_3$ was present. Visible light color emission from 365 nm excitation was blue. Inventive Example 2 demonstrates the formation of $\delta$-phase facial-$Alq_3$ in greater than 99% purity at a low processing temperature.

SAMPLE 8: INVENTIVE EXAMPLE 3

Commercial $Alq_3$ powder was placed on a platinum heating strip and thermally processed. The annealing cycle began at 20° C., the sample was heated at a rate of 10° C./min to 320° C., held at 320° C. for 20 hours, and then cooled at a rate of 50° C./min to 20° C. XRD data were collected at 320° C. at time intervals of 0 min, 5 min, 15 min, 30 min, 1 h, followed by every hour up to 20 h. From analysis of the XRD data it could be determined that the onset of $\delta$-phase $Alq_3$ formation began at 2 hours into the 320° C. processing. After 20 h, the thermally processed powder was analyzed by XRD for phase identification and exposed to 365 nm UV light for evaluation of visible light color emission. XRD phase identification indicated the presence of a mixture of $\delta$-$Alq_3$ and $\gamma$-$Alq_3$. Visible light color emission from a 365 nm excitation was blue. Inventive Example 3 demonstrates the formation of a mixture of $\delta$- and $\gamma$-phase of facial-$Alq_3$ at a very low processing temperature.

SAMPLE 9: INVENTIVE EXAMPLE 4

Commercial $Alq_3$ powder was placed on a platinum heating strip and thermally processed. The annealing cycle began at 20° C., the sample was heated at a rate of 10° C./min to 300° C., held at 300° C. for 20 hours, and then cooled at a rate of 50° C./min to 20° C. XRD data were collected at 300° C. at time intervals of 0 min, 5 min, 15 min, 30 min, 1 h, followed by every hour up to 20 h. From analysis of the XRD data it could be determined that the onset of δ-phase $Alq_3$ formation began at 6 hours into the 300° C. processing. After 20 h, XRD phase identification indicated the presence of a mixture of δ-$Alq_3$, γ-$Alq_3$ and ε-$Alq_3$. Exposure of material closest to the heating strip with 365 nm light resulted in emission of blue light. Exposure of material closest to the beryllium foil with 365 nm light produced a green emission. Inventive Example 4 demonstrates the formation of a mixture of the δ and γ phases of $Alq_3$ phases at a very low processing temperature.

The results for Comparative Example 1-5 and Inventive Examples 1-4 are summarized in Table 1. Commercial β-phase $Alq_3$ powder exhibits green emission when excited with UV-light. Comparative Example 1-5 indicate that thermal processing of $Alq_3$ powders between 365 and 390° C. for short periods of time will provide $Alq_3$ powders that emit blue light but that are mixtures of the γ and δ-phases of $Alq_3$. Inventive Examples 1-2 show that by processing samples for longer periods of time it is possible to obtain a material that emits blue light and is the pure δ-phases of $Alq_3$. Inventive Examples 3-4 demonstrate that blue-light emitting material can be obtained at very low temperatures, below 350° C. The inventive examples also demonstrate that XRD analysis is a useful analytical method for monitoring the process of formation of blue-light emitting $Alq_3$ materials.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

PARTS LIST

A Meridional isomer
B Facial isomer

The invention claimed is:

1. A process for forming the facial isomer of an aluminum trisquinoline complex comprising heating a solid aluminum trisquinoline complex material at a temperature at least 50° C. below the melting point temperature of the solid for a time sufficient to convert the aluminum trisquinoline complex to at least 99 mol % of one polymorph of the facial-isomer that fluoresces with a maximum intensity below 510 nm.

2. A process according to claim 1, wherein the solid is heated at a temperature less than 150° C. below the melting point temperature of the solid.

3. A process according to claim 1, comprising heating the solid material at a temperature at least 60° C. below the melting point temperature of the solid.

4. A process according to claim 1, comprising heating the solid material at a temperature at least 70° C. below the melting point temperature of the solid.

5. A process according to claim 1, comprising heating the solid material at a temperature at least 80° C. below the melting point temperature of the solid.

6. A process according to claim 1, wherein X-ray powder diffraction (XRPD) is used to monitor the conversion to the facial-isomer by periodically measuring the spectra of representative samples.

TABLE 1

SUMMARY OF SAMPLES 1-9

| Sample | Type[1] | Annealing Cycle (° C.) | Heat Rate,[2] ° C./min | Highest Temperture (° C.) | Time Held | Isomer Formed | Phase of $Alq_3$[3] | Color of Light Emission |
|---|---|---|---|---|---|---|---|---|
| 1 | Com-1 | none | — | 20 | — | mer | β | Yellow-Green |
| 1 | Com-1 | none | — | 20 | — | mer | β | Green |
| 2 | Com-2 | 20-350-20 | 10 | 350 | 5 min | mer | ε | Yellow-Green |
| 2 | Com-2 | 20-350-20 | 10 | 350 | 5 min | mer | ε | Green |
| 3 | Com-3 | 20-390-20 | 10 | 390 | 5 min | fac | γ, δ mixture | Blue |
| 4 | Com-4 | 20-350-20 | 10 | 350 | 5 min | fac | γ, δ mixture | Blue |
|   |       | 20-365-20 | 10 | 365 | 1 min |   |   |   |
| 5 | Com-5 | 20-350-390-20 | 10 | 350 | 0 min | fac | γ, δ mixture | Blue |
|   |       |           | 01 | 390 | 0 min |   |   |   |
| 6 | Inv-1 | 20-345-20 | 10 | 345 | 20 hr | fac | δ | Blue |
| 7 | Inv-2 | 20-365-20 | 10 | 365 | 20 hr | fac | δ | Blue |
| 8 | Inv-3 | 20-320-20 | 10 | 320 | 20 hr | fac | γ, δ mixture | Blue |
| 9 | Inv-4 | 20-300-20 | 10 | 300 | 20 hr | mer, fac mixture | ε, γ, δ mixture | Blue and Green |

[1]Com refers to comparison, Inv refers to inventive.
[2]All samples were cooled at a rate of 50° C./min.
[3]Determined by XRD Analysis.

7. A process according to claim 1, wherein the aluminum trisquinoline complex is tris(2-methyl-8-quinolinolato)aluminum(III).

8. A process according to claim 6, wherein the polymorph formed is the δ-phase of facial-tris(2-methyl-8-quinolinolato)aluminum(III).

9. A process according to claim 6, comprising heating tris(2-methyl-8-quinolinolato)aluminum(III) at a temperature below 370° C. to form greater than 99% of the δ-phase of facial-tris(2-methyl-8-quinolinolato)aluminum(III).

10. A process according to claim 6, comprising heating tris(2-methyl-8-quinolinolato)aluminum(III) at a temperature below 360° C. to form greater than 99% of the δ-phase of facial-tris(2-methyl-8-quinolinolato)aluminum(III).

11. A process according to claim 6, comprising heating tris(2-methyl-8-quinolinolato)aluminum(III) at a temperature below 350° C. to form greater than 99% of the δ-phase of facial-tris(2-methyl-8-quinolinolato)aluminum(III).

12. A process for forming the facial-isomer of an aluminum trisquinoline complex comprising heating the solid aluminum trisquinoline complex material at a temperature below 340° C. for a time sufficient to form the facial-isomer, wherein the facial-isomer formed fluoresces with a maximum intensity below 510 nm.

13. A process according to claim 12, wherein the solid material is heated at a temperature above 300° C.

14. A process according to claim 12 wherein the solid material is heated for a time sufficient to convert the solid to at least 99% of the facial-isomer.

15. A process according to claim 12, wherein the aluminum trisquinoline complex is tris(2-methyl-8-quinolinolato)aluminum(III).

16. A process according to claim 15, wherein the tris(2-methyl-8-quinolinolato)aluminum(III) is converted to at least 99% of the facial-isomer.

17. A process according to claim 15, wherein a mixture of the γ- and δ-phases of tris(2-methyl-8-quinolinolato)aluminum(III) are formed.

18. A process according to claim 15, wherein at 99% of the δ-phases of facial-tris(2-methyl-8-quinolinolato)aluminum(III) is formed.

19. A process according to claim 15, wherein tris(2-methyl-8-quinolinolato)aluminum(III) is heated for up to 48 hours.

* * * * *